United States Patent [19]

Gottlieb

[11] Patent Number: 4,571,093

[45] Date of Patent: Feb. 18, 1986

[54] METHOD OF TESTING PLASTIC-PACKAGED SEMICONDUCTOR DEVICES

[75] Inventor: G. Eugene Gottlieb, East Brunswick, N.J.

[73] Assignee: Burroughs Corporation, Detroit, Mich.

[21] Appl. No.: 548,611

[22] Filed: Nov. 4, 1983

[51] Int. Cl.⁴ .............................................. G01N 13/00
[52] U.S. Cl. .................................... 374/57; 73/432 SD
[58] Field of Search ............... 73/38, 76, 73, 40, 49.2, 73/49.3, 52, 432 SD, 29; 29/574; 357/72; 374/57

[56] References Cited

U.S. PATENT DOCUMENTS

| | | | |
|---|---|---|---|
| 3,913,217 | 10/1975 | Misawa et al. | 29/580 |
| 3,996,602 | 12/1976 | Goldberg et al. | 357/72 |
| 4,001,872 | 1/1977 | Khajezadeh | 357/72 |
| 4,248,920 | 2/1981 | Yoshizumi et al. | 357/70 |
| 4,365,264 | 12/1982 | Mukai et al. | 357/73 |

Primary Examiner—S. Clement Swisher
Assistant Examiner—Hezron E. Williams
Attorney, Agent, or Firm—Robert A. Green; Kevin R. Peterson; Mark T. Starr

[57] ABSTRACT

The method of testing the moisture ingression rate of semiconductor devices encapsulated in plastic packages comprising first treating the devices in a pressure cooker at elevated temperature and immediately thereafter treating said devices in an 85° C. temperature and 85% humidity atmosphere for a time.

4 Claims, 1 Drawing Figure

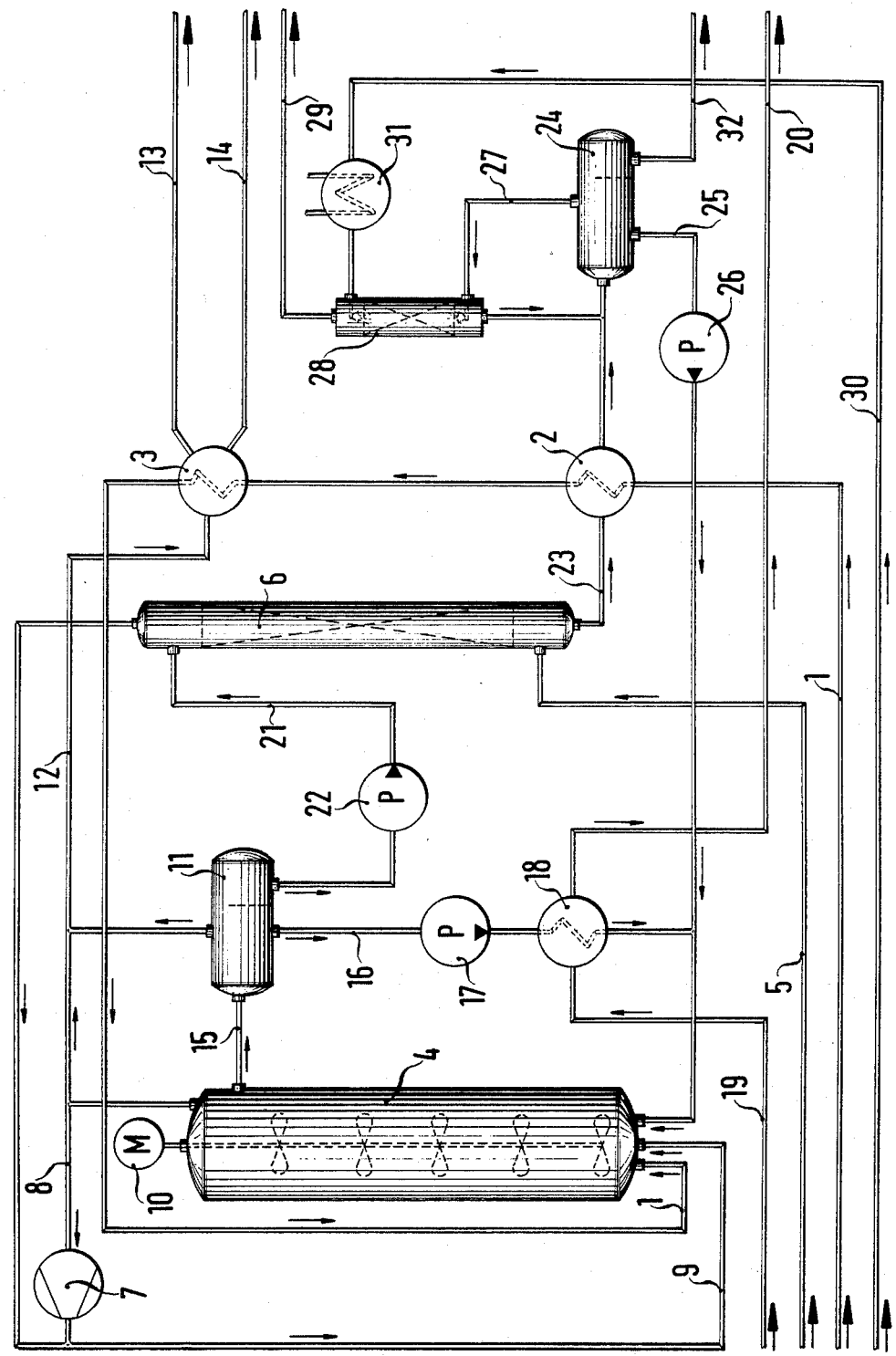

METHOD OF TESTING PLASTIC-PACKAGED SEMICONDUCTOR DEVICES

BACKGROUND OF THE INVENTION

With the advent of integrated circuits, electronic devices of this type have been encapsulated in various plastic materials to form low cost, easily handled packages. Since these plastic encapsulants are not moisture resistant, moisture related failures are the primary problems encountered in utilizing plastic-packaged devices. Extensive T-H (temperature-humidity) testing is commonly used in order to minimize these types of problems.

In the past, these devices have been tested, some by pressure cooker heating and some by separate 85/85 (85° C. and 85% relative humidity) testing. These two separate procedures have been the standard techniques for the evaluation of plastic-packaged semiconductor devices, primarily because these methods are simple, reliable and relatively reproducible. The primary failure mechanisms in pressure cooker testing are chemical corrosion and threshold shifts, while the primary failure mechanism in 85/85 testing is electrolytic corrosion. Improvements in both device processing and passivation, and plastic encapsulants and molding techniques have significantly improved the reliability of plastic-packaged devices, and, therefore, longer 85/85 testing time of 1000-2000 hours are often required. For this reason, there have been several efforts to develop more accelerated testing techniques in order to decrease what has developed into excessive 85/85 test times. However, none of these is completely satisfactory.

The present invention provides an optimum method of accelerating the testing of plastic-encapsulated devices by increasing the moisture ingression rate by means of a sequential procedure that utilizes pressure cooker conditions to rapidly drive the moisture to the die surface, followed by 85/85 to produce electrolytic corrosion. This technique is entitled Pressure Cooker and Temperature Humidity or PCTH processing.

DESCRIPTION OF THE INVENTION

The principles of the present invention have broad application to plastic-packaged semiconductor devices although the specific techniques described below were developed for MOS 16 Kb dynamic RAMs. Several different synthetic resin or plastic encapsulants with silica fillers were evaluated. The general procedure consisted of treating parts in a pressure cooker for 24-96 hours, electrically testing, and then placing the survivors into 85/85 Atmosphere. Several different pressure cooker times and temperatures were studied. Since the standard pressure cooker conditions are 121° C. for 96 hours, this was also the original condition. In order to obtain further decreases in the test times, higher temperatures such as 130° C. for varying time periods were also studied, as discussed below. Since the pressure cooker conditions are univariant, they can be controlled by specifying either the temperature or the pressure. It was found that temperature control is not only easier but also more accurate and, therefore, the pressure cooker part of the process was performed by putting the pressure cooker into a precisely controlled oven. Additional control was obtained by monitoring the temperature inside the pressure cooker via an internal thermocouple connected to lead through connectors for readouts. The pressure was also monitored via a pressure gauge connected to the system.

The logistics of transferring the parts from the pressure cooker to the 85/85 chamber is also an important consideration. It was found that rapid moisture desorption can occur at room temperature and, therefore, it is important that the electrical evaluation be performed quickly, and the parts placed into the 85/85 chamber as soon as possible. It appears that, if this cannot be completed within four hours, the parts must be stored in a high humidity chamber.

The primary variable in the PCTH technique is the pressure cooker condition used. A wide range of temperatures and times are possible, starting at 121° C., with the practical upper limit being the $T_G$ of the particular plastic composition. It was found that 96 hours of pressure cooker at 121° C., followed by 100 hours of 85/85, or 24 hours of pressure cooker at 130° C., followed by 50 hours of 85/85 give satisfactory reproducible results. Both of these conditions represent dramatic decreases from the industry standard of 1000-2000 hours of 85/85.

The philosophical foundation of the PCTH technique is based on the fact that moisture must reach the die surface before moisture related failures can be observed. Therefore, in order to decrease test times, we must accelerate the rate at which the moisture diffuses to the die surface. The pressure cooker is an effective way to do this, and Fick's First Law is the explanation. This law states that the quantity of diffusing material which passes through a unit area normal to the direction of diffusion per unit time is proportional to its concentration gradient (similar to Ohms law for current and Fouriers law for heat flow). Mathematically this is stated as $$J = -D(\delta C/\delta X)$$

where C=concentration, X is the direction of diffusion, J is the flux, and D is the diffusion coefficient. At 121° C. the equilibrium water vapor pressure (concentration) is 1537 mm, while at 85° C. it is about 370 mm. This is a 4.1× difference in H₂O concentration. Furthermore, the diffusion coefficient is much larger at 121° C., than at 85° C., again having an accelerating effect on the rate at which moisture diffuses to the die surface. These facts are supported by the relative weight gains and provide a model for the accelerating effects of the PCTH technique.

In order to produce further acceleration in the PCTH technique, a series of experiments were performed using 130° C. pressure cooker pretreatments, for varying time periods, followed by 50 hours of 85/85. The objective was to decrease the total test time from about 192 hours required for the 121° C. technique described above. According to Fick's Law, the higher temperature and the higher equilibrium water vapor concentration should have the desired effect.

It has also been found that 48 hours of 85/85 treatment is sufficient, since there is very little additional fallout during the next 48 hours, especially when the 24 hour pressure cooker pretreatment is used. This data indicated that 48 hours of pressure cooker pretreatment was too severe in most cases. The reason for the sharp divergence in results between 24 and 48 hour pressure cooker pretreatment is not completely clear. As would be expected, the 48 hour pretreatment produces a somewhat larger weight gain, but the difference is not significant enough to explain the dramatic difference in the results, Nevertheless, these results indicate that a 24 hour pressure cooker pretreatment followed by 48 hours of 85/85 are usable PCTH conditions.

According to the invention, parts to be tested are put into a pressure cooker for 24–96 hours, followed by 50–100 hours of 85/85. Weight gain measurements are performed on parts pretreated at several combinations of pressure cooker temperatures and times, and compared with parts placed directly into an 85/85 chamber. In all cases, the pressure cooker pretreated parts gain about 5× as much weight as the parts put directly into 85/85. These results are consistent with experimental observations that very few failures occur in 85/85 until about 500 hours of testing. Even though the pressure cooker pretreated parts lose weight when they are put into the 85/85 chamber, and eventually come to equilibrium with parts placed directly into 85/85, during the first 50–100 hours of testing, these parts are in a moisture concentration up to 10× higher than normal 85/85.

It is noted that, in practicing the invention, a wide range of pressure cooker pretreatment time/temperature combinations are possible. The two specific conditions described above can decrease the required testing times from about 1000 hours to 72–192 hours. In addition, the invention can be practiced with all types of plastic-packaged devices, with each plastic having its own moisture resistance characteristic.

What is claimed is:

1. The method of life-testing semiconductor devices encapsulated in plastic packages by speeding up the moisture ingression rate comprising the steps of
    assembling a group of plastic-encapsulated semiconductor devices,
    treating said devices in a pressure cooker for a time in the range of about 24 to about 96 hours at a temperature in the range of about 130° C. to about 121° C., and
    thereafter submitting said devices to an 85° C. temperature and 85% humidity for a time in the range of about 50 to about 100 hours.

2. The method of life-testing semiconductor devices encapsulated in plastic packages by speeding up the moisture ingression rate comprising the steps of
    assembling a group of plastic-encapsulated semiconductor devices,
    treating said devices in a pressure cooker for a time of about 24 hours at a temperature of about 130° C., and
    thereafter submitting said devices to 85° C. temperature and 85% humidity for a time of about 50 hours.

3. The method of life-testing semiconductor devices encapsulated in plastic packages by speeding up the moisture ingression rate comprising the steps of
    assembling a group of plastic-encapsulated semiconductor devices,
    treating said devices in a pressure cooker for a time of about 96 hours at a temperature of about 121° C., and
    thereafter submitting said devices to 85° C. temperature and 85% humidity for a time of about 100 hours.

4. The method of life-testing semiconductor devices encapsulated in plastic packages by speeding up the moisture ingression rate comprising the steps of
    assembling a group of plastic-encapsulated semiconductor devices,
    treating said devices in a pressure cooker for a selected time period at an elevated temperature to drive moisture into the devices, and
    thereafter submitting said devices to 85° C. temperature and 85% humidity for a selected time.

* * * * *

UNITED STATES PATENT AND TRADEMARK OFFICE
CERTIFICATE OF CORRECTION

PATENT NO. : 4,571,093

DATED : February 18, 1986

INVENTOR(S) : C. Eugene Gottlieb

It is certified that error appears in the above-identified patent and that said Letters Patent is hereby corrected as shown below:

The title page should be deleted to appear as per attached title page.

Signed and Sealed this

Tenth Day of June 1986

[SEAL]

Attest:

DONALD J. QUIGG

Attesting Officer

Commissioner of Patents and Trademarks

United States Patent [19]

Gottlieb

[11] Patent Number: 4,571,093
[45] Date of Patent: Feb. 18, 1986

[54] METHOD OF TESTING PLASTIC-PACKAGED SEMICONDUCTOR DEVICES

[75] Inventor: G. Eugene Gottlieb, East Brunswick, N.J.

[73] Assignee: Burroughs Corporation, Detroit, Mich.

[21] Appl. No.: 548,611

[22] Filed: Nov. 4, 1983

[51] Int. Cl.³ .............................................. G01N 13/00
[52] U.S. Cl. .................................. 374/57; 73/432 SD
[58] Field of Search ............... 73/38, 76, 73, 40, 49.2, 73/49.3, 52, 432 SD, 29; 29/574; 357/72; 374/57

[56] References Cited

U.S. PATENT DOCUMENTS

| | | | |
|---|---|---|---|
| 3,913,217 | 10/1975 | Misawa et al. | 29/580 |
| 3,996,602 | 12/1976 | Goldberg et al. | 357/72 |
| 4,001,872 | 1/1977 | Khajezadeh | 357/72 |
| 4,248,920 | 2/1981 | Yoshizumi et al. | 357/70 |
| 4,365,264 | 12/1982 | Mukai et al. | 357/73 |

Primary Examiner—S. Clement Swisher
Assistant Examiner—Hezron E. Williams
Attorney, Agent, or Firm—Robert A. Green; Kevin R. Peterson; Mark T. Starr

[57] ABSTRACT

The method of testing the moisture ingression rate of semiconductor devices encapsulated in plastic packages comprising first treating the devices in a pressure cooker at elevated temperature and immediately thereafter treating said devices in an 85° C. temperature and 85% humidity atmosphere for a time.

4 Claims, No Drawings